United States Patent [19]

Steffee

[11] Patent Number: 4,642,122
[45] Date of Patent: Feb. 10, 1987

[54] TOE IMPLANT

[75] Inventor: Arthur D. Steffee, Gates Mills, Ohio

[73] Assignee: Laure Prosthetics, Inc., Portage, Mich.

[21] Appl. No.: 847,362

[22] Filed: Apr. 2, 1986

[51] Int. Cl.$^4$ ............................................. A61F 2/42
[52] U.S. Cl. .................................................... 623/21
[58] Field of Search ............................ 623/21, 18, 20

[56] References Cited

U.S. PATENT DOCUMENTS

| 3,946,445 | 3/1976 | Bentley et al. | 623/21 X |
|---|---|---|---|
| 4,156,296 | 5/1979 | Johnson et al. | 623/21 |
| 4,231,121 | 11/1980 | Lewis | 623/21 |
| 4,242,759 | 1/1981 | White | 623/21 |
| 4,245,359 | 1/1981 | Stuhmer | 623/18 X |
| 4,367,562 | 1/1983 | Gauthier | 623/18 |
| 4,375,703 | 3/1983 | Evans et al. | 623/21 |

*Primary Examiner*—Ronald L. Frinks
*Attorney, Agent, or Firm*—Flynn, Thiel, Boutell & Tanis

[57] ABSTRACT

An implantable joint for replacing a human toe joint. The joint includes a one-piece tack member implantable into the distal end of a metatarsal, and a one-piece socket member implantable into the proximal end of a phalanx. The tack member has an enlarged head defining a smooth part-spherical convex bearing surface which engages a smooth part-spherical concave bearing surface on an enlarged head of the socket member. The head of the socket member is elliptical in cross section so that the concave bearing surface extends through about 90° in the vertical direction. The convex bearing surface of the tack member is nonsymmetrical relative to the longitudinal axis and extends through an angle which closely approximates 180°, with this bearing surface projecting downwardly from the horizontal longitudinal axis through an extent greater than 90°. Each of the members has a stem which projects for engagement within the respective bone, the stems being disposed with their longitudinal axes extending generally parallel with but disposed downwardly from the longitudinal axes of the respective head parts.

3 Claims, 5 Drawing Figures

TOE IMPLANT

FIELD OF THE INVENTION

This invention relates to a prosthetic device for replacement of a joint in a human being and, more specifically, to an improved implantable toe joint.

BACKGROUND OF THE INVENTION

Numerous prosthetic joints have been developed for replacing joints in human bodies, including joints for the toes and fingers. Many of these joints involve a ball-and-socket connection wherein two joint parts are physically held or joined together in a swiveling relationship, with such joints requiring the two parts to be physically snapped or joined together during the implanting operation. Such connection, however, can be difficult to perform, particularly when replacing small joints such as toe joints.

In an effort to provide a small joint which does not require such connection, various implantable joints have been proposed wherein the two joint parts have opposed head and socket parts which provide a swivel or swingable connection, but which do not require a physical joining of the two parts together. Most of these prior attempts, however, have proven less than desirable for various reasons. For example, some of the known joints have not provided proper mating and swiveling relationship between the joint parts in order to accurately reproduce the necessary natural swiveling movement of the joint being replaced. Others of these known joints have provided structural or geometrical features which have been less than optimum with respect to either surgically implanting the joint and/or replacing the natural joint structure and its inherent function.

Examples of prior art joints are illustrated by U.S. Pat. Nos. 4,156,296, 4,231,121, 4,367,562, 4,242,759 and 3,946,445.

Accordingly, it is an object of this invention to provide an improved prosthesis joint, specifically an implantable joint for replacing the human toe joint, which implantable joint is for connection between the metatarsal and middle phalangeal bones and provides a functional cooperation which closely depicts the desired and permissible movements of the natural joint.

In the improved implantable toe joint of this invention, there are provided two one-piece members, namely a tack member of metal which is implanted into the end of the metatarsal, and a socket member of plastics which is implanted into the adjacent end of the middle or proximal phalange. The tack member has a smooth convex part-spherical bearing surface which is adapted to freely slidably contact a smooth concave part-spherical bearing surface on the socket member, these two bearing surfaces being generated about the same radius. The convex bearing surface on the tack member extends symmetrically sidewardly in opposite directions through an angle which approaches but is less than 180°, and this convex bearing surface extends upwardly through an angle less than 90° but downwardly through an angle substantially in excess of 90° so that the tack member has an enlarged head portion which defines thereon the bearing surface. This head portion has a lower rearwardly projecting extension to provide smooth arcuate sliding between the joint members over a permissible range while providing positive contact support between the joint members throughout the swiveling range. The tack member has a substantially cylindrical stem projecting rearwardly from the head portion for implantation into the metatarsal, this stem being of a decreasing tapered cross section as it projects rearwardly. The longitudinal axis of the stem is positioned in downwardly spaced but substantially parallel relationship relative to the longitudinal axis of the head portion, with the former longitudinal axis being substantially concentrically aligned with the longitudinal axis of the metatarsal. The socket member has a head part which defines a concave bearing surface thereon, this head part being of a substantially horizontally elongated transverse cross section so that the concave bearing surface has an arcuate extent in the vertical direction which is rather small in relationship to the vertical arcuate extent of the convex bearing surface so as to permit substantial vertical swiveling between the tack and socket members when implanted. The head part of the socket member, and more specifically the concave bearing surface, extends sidewardly or horizontally through an arcuate extent which is similar to but preferably slightly smaller than the horizontal arcuate extent of the convex bearing surface. The head part of the socket member has a stem portion which projects outwardly for implantation into the phalange. The stem portion has a plurality of axially spaced annular ribs or flanges associated therewith, these flanges being resiliently deflectable to effect a self-holding or locking of the socket member to the phalange when implanted thereon.

Other objects and purposes of the invention will be apparent to persons familiar with joints of this general type upon reading the following specification and inspecting the accompanying drawings.

Figure 5:
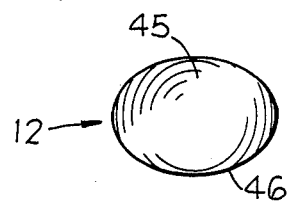
FIGS. 3, 4 and 5 are views taken substantially along lines III—III, IV—IV and V—V, respectively, as appearing in FIG. 1.
Figure 4:
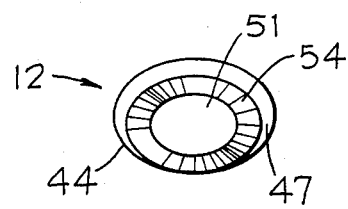

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the joint and designated parts thereof. Said terminology will include the words specifically mentioned, derivatives thereof, and words of similar import.

DETAILED DESCRIPTION

Figure 2:
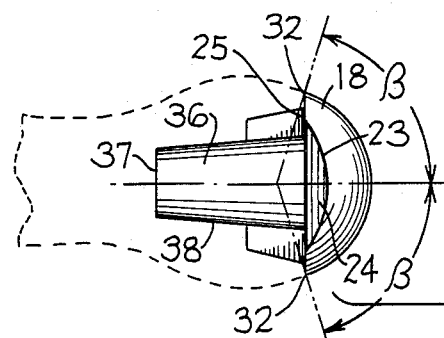
FIG. 2 is a top view of the joint as appearing in FIG. 1.
Figure 2:
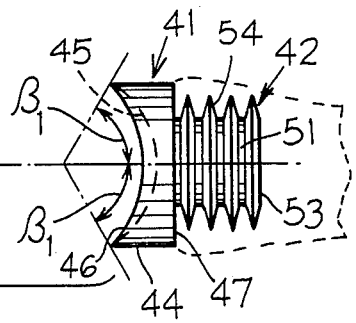
Figure 1:
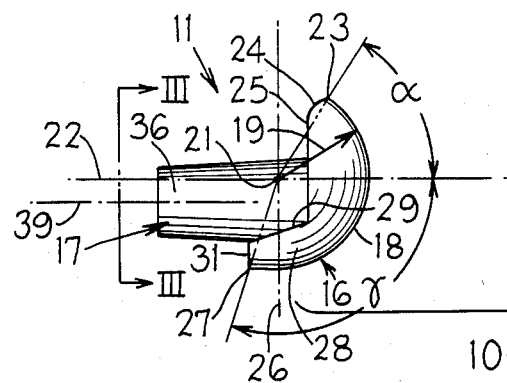
FIG. 1 is a side elevational view which illustrates the joint of the present invention with the socket and tack members shown in separated condition to facilitate illustration thereof.
Figure 1:
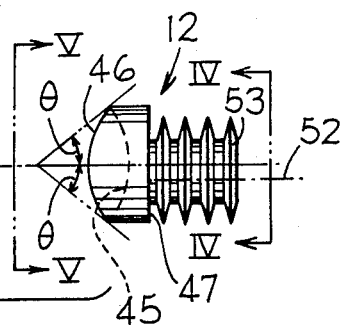

Referring to the drawings, and specifically FIGS. 1 and 2, there is illustrated a prosthetic or implantable joint 10 which is designed specifically for replacing a human toe joint, namely the joint between the metatarsal and the middle phalange. This joint 10 is created by two members which do not structurally join together, namely a one-piece headed member 11 which will hereinafter be referred to as a "tack member", and a one-piece socket member 12. The tack member 11 is normally constructed of metal, such as a chrome cobalt alloy, and is adapted to be implanted into the outer or distal end of the metatarsal. The socket member 12 is normally constructed of a plastics material, such as a high-density polyethylene material having a sufficient self-lubricating property, and is adapted to be implanted into the inner or proximal end of the adjacent phalanx.

Considering first the structure of the tack member 11, it includes an enlarged head part 16 having a stem part 17 projecting rearwardly therefrom.

Figure 3:
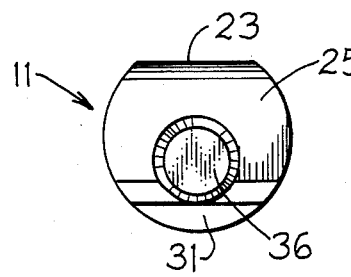

The head part 16 defines on the outer face thereof a smooth, part-spherical, convex bearing surface 18. This latter surface 18 is generated about a radius 19 having a center point 21 which is located on the longitudinal axis 22 of the head part. The convex bearing surface 18 as generated about this center point 21 projects upwardly through an angle $\alpha$ which is significantly less than 90°, this angle $\alpha$ typically being in the range of 55°–65°, whereby this convex bearing surface 18 terminates in an upper extremity or edge 23 which lies substantially within a horizontal plane as illustrated in FIG. 3 so as to effectively flatten the upper portion of the head part, although this upper edge or extremity 23 in effect defines a rearwardly directed arc as appearing in FIG. 2. The head part at this upper edge 23 is provided with a rounded surface 24 which projects rearwardly and inwardly so as to terminate in a planar rear surface 25, the latter extending substantially perpendicularly with respect to the longitudinal axis 22 but being spaced forwardly from the center point 21.

The bearing surface 18 as generated by radius 19 about center point 21 swings downwardly from the axis 22 through an angle $\gamma$ which significantly exceeds 90°, this (angle $\gamma$ typically being in the range of 110°–120°. The lower portion of this convex bearing surface terminates in a lower extremity or edge 27 which is located rearwardly from the perpendicular plane 26 which passes through the center point 21. This hence results in the head part 16 being provided with a rearward extension 28 associated with the lower portion thereof, this rearward extension 28 projecting rearwardly from the rear planar surface 25 to a point located past the plane 26. This rearward extension 28 has a substantially planar upper surface 29 which is spaced downwardly a substantial extent from the axis 22, with this surface 29 extending from the rear surface 25 and being slightly downwardly sloped as it projects rearwardly so as to terminate at the rear surface 31. This hence results in the head part 16, when viewed from the side, having a substantially L-shaped configuration.

The convex bearing surface 18, when viewed either from above or below, extends symmetrically in opposite sideward directions from the axis 22 through angles $\beta$, which angles $\beta$ are less than 90° and are preferably in the range of about 65°–75°. The sideward generation of the convex surface 18 terminates at the side extremities 32, the latter being effectively defined in the plane of the rear surface 25.

The stem part 17 of the tack member 11 is formed substantially as a cylindrical pin 36 which projects rearwardly from the rear surface 25 in substantially perpendicular relationship thereto. This cylindrical tack pin 36 projects rearwardly through an axial extent which is substantially greater than the thickness of the head part as measured directly along the axis 22, whereupon the pin 36 terminates in a free end surface 37. Pin 36 is preferably provided with a tapered or conical sidewall 38 which is of progressively decreasing diameter as the pin projects rearwardly so as to facilitate the insertion of the pin 36 into the metatarsal. The pin 36 is generated about a longitudinal centerline 39 which, while it extends parallel with the axis 22, is nevertheless spaced downwardly from the axis 22 so that the pin 36 is eccentrically displaced downwardly relative to the head part as appearing in FIGS. 1 and 3. This axis 99 is substantially aligned with the longitudinal central axis of the metatarsal and phalanx when the joint is implanted into the toe. The pin 36, at the lower portion thereof, merges into the rearward extension 28 of the head part.

Considering now the socket member 12, it also is formed by two primary parts, namely a head part 41 and a stem part 42.

The head part 41, when viewed in perpendicular cross section relative to the longitudinal axis 22, has a substantially elliptical cross section, whereby the head part 41 has an outer peripheral surface 44 which is substantially elliptical when viewed in transverse cross section. The elliptical cross section is horizontally or sidewardly elongated in that the major axis of the ellipse extends substantially horizontally, and conversely the narrow dimension as defined by the minor axis of the ellipse extends substantially vertically. The longitudinal axis 22 extends substantially through the center of the ellipse defined by the head part 41.

This head part 41 defines, on the front or end face thereof, a smooth, part-spherical, concave bearing surface 45 which terminates in an outer edge 46, the latter being defined substantially at the outer peripheral surface 44 but, due to the generally elliptical configuration of this latter surface, the edge 46 is nonplanar.

The concave bearing surface 45 is, like the surface 18, generated on the same radius 19 and is generated about a center point located on the axis 22. The concave bearing surface 45 is symmetrically sidewardly generated about the axis 22 through angles $\beta_1$, which latter angles closely approach but are normally a few degrees smaller than the angles $\beta$ associated with the sideward extent of the convex bearing surface 18. Vertically, however, the concave bearing surface 45 is symmetrically generated both upwardly and downwardly through angles $\theta$ relative to the axis 22, with the angle $\theta$ being significantly smaller than the angles $\alpha$ or $\gamma$. In fact, the angle $\theta$ preferably is in the range of about 40°–50°, so that the concave bearing surface 45 hence preferably extends through a vertical angle (as measured by 2 $\theta$) of about 90°. The presence of this concave bearing surface 45 results in the head part 41 defining a shallow recess of substantially elliptical cross section being formed in the end face thereof, which recess accommodates therein a portion of the head part 16 as explained hereinafter.

The head part 41 of the socket member terminates in a substantially planar rear surface 47 which extends transversely relative to the axis 22, and the stem part 42 projects axially outwardly away from this rear surface 47. This stem part 47 includes an outwardly projecting pin 51 which is disposed in eccentric relationship relative to the center part in that the longitudinally extending centerline 52 of the pin 51 is positioned parallel to but spaced downwardly from the axis 22. This pin 51 is also of elliptical cross section, which elliptical cross section is horizontally elongated consistent with the horizontally elongated orientation of the head part 41. The pin 51 projects outwardly through an axial extent so as to terminate in a rear surface 53, with the pin 51 having an axial extent which is greater than the axial dimension of the head part 41. Pin 51 also has a plurality of axially spaced annular flanges 54 formed thereon and projecting radially outwardly therefrom. These flanges 54 are of a generally V-shaped or tapered cross section as they project outwardly so as to effectively narrow down to a point, whereupon the flanges 54 are hence sufficiently resiliently deflectable or deformable to permit them to be suitably deflected when inserted into the end of the phalanx to permit self-locking of the socket member thereto.

OPERATION

While the implantion and operation of the joint 10 is believed apparent from the description set forth above, nevertheless same will be briefly described to ensure a complete understanding thereof.

To implant the joint 10, the adjacent joint ends of the metatarsal and phalanx are surgically removed so as to define substantially flat end surfaces which can effectively abut against the rear surfaces of the implant members 11 and 12. The socket member 12 is appropriately inserted into the proximal end of the phalanx, with the insertion and securing of the socket member greatly facilitated by the presence of the resilient locking flanges 54, although it is also normally preferred to additionally utilize bone seed to assist in fixedly securing the stem within the phalanx. The tack member 11 is similarly surgically secured to the metatarsal by inserting the stem pin 36 into the metatarsal. The members 10 and 11 are then positioned so that the bearing surfaces 18 and 45 can smoothly slidably rotate one upon the other. The tack member 11 is oriented so that the extension 28 thereof is disposed lowermost, and this permits the head part 41 of the socket member to freely slidably move, particularly vertically, along the convex bearing surface 18. The configuration of bearing surface 18 permits some upward pivoting of the socket member, although this is necessarily of lesser extent consistent with the natural movement of the toe joint in this direction. However, the significant downward extension of the surface 18 through the angle γ permits the socket member 12 and the phalanx joined thereto to swivel or swing downwardly through a substantial arcuate extent consistent with the substantial range permitted by the natural toe joint. At the same time, even though the implanted joint 10 permits this downward swinging movement through a substantial angle, nevertheless the head part 41 remains firmly in slidable and supportive contact with the bearing surface 18 at all times inasmuch as the lower extension 28 thereof extends substantially beyond 90° and hence readily accommodates the full range of natural toe movement. The cooperation between the bearing surfaces 18 and 45 also permits limited sideward swinging of the socket member 12 consistent with natural toe movement, although this sideward displacement is obviously of very small extent, again consistent with the permissible movement of the natural toe joint.

The improved joint of the present invention thus provides for a significant range of movement between the phalanx and metatarsal so that the implanted joint provides a range which is believed more consistent with the natural toe joint. The range of the improved joint of this invention is hence believed greater than permissible with prior prosthetic joints, and at the same time the present invention permits this greater range of movement to occur while providing substantially greater control and slidable contact between the cooperating joint members.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. In a prosthetic toe joint adapted for replacing a human toe joint, including a one-piece tack member for implanting into the distal end of a metatarsal, and a one-piece socket member for implanting into the proximal end of a phalanx, the improvement comprising:

said tack member having an enlarged head part provided with a smooth, part-spherical, convex bearing surface thereon, and a stem part fixed to said head part and projecting in a direction away from said convex bearing surface, said convex bearing surface being generated about a radius having a center point located on a longitudinal axis which functions as the central longitudinal axis of the head part, said convex bearing surface extending upwardly above said axis and symmetrically sidewardly on opposite sides of said axis through first angles less than 90°, and said convex bearing surface projecting downwardly from said axis through a second angle greater than 90°, said head part having a substantially planar rear surface which extends transversely with respect to said axis and intersects said axis at a location disposed forwardly of said center point, said rear surface extending vertically from the uppermost edge of said head part to a location disposed downwardly below said axis, said head part having a lower portion which is disposed downwardly a substantial distance below said axis and which extends rearwardly from said rear surface to a point located rearwardly of a plane which perpendicularly intersects said axis at said center point, said lower portion defining thereon a lower and rearward extension of said convex bearing surface, said stem part comprising a pinlike member which is integrally fixed to said head part and projects rearwardly from said rear surface, said pinlike member projecting axially rearwardly a substantial distance beyond said lower portion of said head part, said pinlike member having a central longitudinally extending axis which is generally parallel to but spaced downwardly below the longitudinal axis of said head part;

said socket member being constructed of a plastics material and having a head part at one end thereof, said head part on the free end thereof defining a smooth, part-spherical, concave bearing surface, and a stem part fixed to said head part and projecting axially outwardly away from the other end thereof, said head part having an outer annular surface which is generally elliptical in cross section, said elliptical cross section being elongated horizontally so that the minor or small dimension of the ellipse extends generally vertically, said concave bearing surface being defined by an edge surface where the concave bearing surface intersects said peripheral surface, said edge surface being of a generally horizontally elongated elliptical profile, said head part having a longitudinal centerline which passes through the center of the elliptical cross section and is substantially aligned with the longitudinal axis of the head part of said tack member, said concave bearing surface being generated about a second radius having a center located on said longitudinal centerline, said second radius being substantially equal to said first radius, said concave bearing surface extending symmetrically horizontally sidewardly in opposite directions through third angles which are less than 90° and which are slightly less than said first angles, and said concave bearing surface extending vertically in opposite directions from said longitudinal centerline through fourth angles which are significantly less than said first angles, said stem part including a pinlike element which projects outwardly from the other end of said head part and is provided with a plurality of annular flexible ribs disposed thereon in axially spaced relation, said pinlike element and said ribs being of a generally horizontally elongated elliptical configuration.

2. A joint according to claim 1, wherein the pinlike element of said socket member has a longitudinally extending centerline which is substantially parallel with but spaced downwardly from the longitudinal centerline of the head part of said socket member.

3. A joint according to claim 1, wherein said first angle is smaller than said second angle, wherein said second angle is in the range of about 110°–120°, and wherein said fourth angle is in the range of 40°–50°.

* * * * *